United States Patent
Shelton, IV et al.

(10) Patent No.: US 10,925,601 B2
(45) Date of Patent: Feb. 23, 2021

(54) SURGICAL END EFFECTOR ADJUNCT ATTACHMENT

(71) Applicant: Ethicon LLC, Guaynabo, PR (US)

(72) Inventors: Frederick E. Shelton, IV, Hillsboro, OH (US); Jason L. Harris, Lebanon, OH (US); Michael J. Vendely, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 638 days.

(21) Appl. No.: 15/435,986

(22) Filed: Feb. 17, 2017

(65) Prior Publication Data

US 2018/0235613 A1 Aug. 23, 2018

(51) Int. Cl.
| A61B 17/072 | (2006.01) |
| A61B 17/04 | (2006.01) |
| A61B 17/115 | (2006.01) |

(52) U.S. Cl.
CPC ........ A61B 17/072 (2013.01); A61B 17/0467 (2013.01); A61B 17/07207 (2013.01); A61B 17/07292 (2013.01); A61B 17/1155 (2013.01); A61B 2017/07214 (2013.01); A61B 2017/07257 (2013.01); A61B 2017/07271 (2013.01)

(58) Field of Classification Search
CPC ........ A61B 17/07207; A61B 17/07292; A61B 17/1155; A61B 17/07214; A61B 17/07257; A61B 17/07271; A61B 17/0467; A61B 17/072; A61B 2017/07214; A61B 2017/07257; A61B 2017/07271
USPC ..................................................... 227/176.1
See application file for complete search history.

(56) References Cited

U.S. PATENT DOCUMENTS

| 7,143,925 | B2 | 12/2006 | Shelton, IV et al. |
| 7,601,118 | B2 | 10/2009 | Smith et al. |
| 8,317,070 | B2 | 11/2012 | Hueil et al. |
| 8,393,514 | B2 | 3/2013 | Shelton, IV et al. |
| 9,282,962 | B2 | 3/2016 | Schmid et al. |
| 2009/0134200 | A1* | 5/2009 | Tarinelli ........... A61B 17/07207 227/180.1 |
| 2010/0252612 | A1* | 10/2010 | Viola ............... A61B 17/07207 227/180.1 |
| 2013/0221065 | A1 | 8/2013 | Aronhalt et al. |
| 2013/0256377 | A1 | 10/2013 | Schmid et al. |

(Continued)

FOREIGN PATENT DOCUMENTS

| EP | 705570 A1 | 4/1996 |
| EP | 2630922 A1 | 8/2013 |

OTHER PUBLICATIONS

Extended European Search Report for EP App. No. 18157126.6 dated May 15, 2018 (11 pages).

*Primary Examiner* — Chelsea E Stinson
*Assistant Examiner* — Mary C Hibbert-Copeland
(74) *Attorney, Agent, or Firm* — Mintz Levin Cohn Ferris Glovsky and Popeo, P.C.

(57) ABSTRACT

Various embodiments of a surgical end effector are provided. The end effector can include upper and lower jaws, and an anvil assembly configured to be releasably coupled to the upper and/or lower jaws. The anvil assembly can include an anvil plate that mates and aligns with the jaw, and staple pockets that align with staple cavities formed in the cartridge for formed staples fired from the cartridge. An adjunct material can be releasably secured to either the cartridge or anvil assembly, such as with one or more sutures.

19 Claims, 12 Drawing Sheets

(56) References Cited

U.S. PATENT DOCUMENTS

| | | |
|---|---|---|
| 2014/0131418 A1* | 5/2014 | Kostrzewski .......... A61B 17/32 227/176.1 |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0134077 A1 | 5/2015 | Shelton, IV et al. |
| 2015/0272575 A1 | 10/2015 | Leimbach et al. |
| 2015/0277471 A1 | 10/2015 | Leimbach et al. |
| 2015/0351758 A1 | 12/2015 | Shelton, IV et al. |
| 2016/0058451 A1 | 3/2016 | (Tarinelli) Racenet et al. |
| 2016/0089142 A1 | 3/2016 | Harris et al. |
| 2017/0055986 A1 | 3/2017 | Harris et al. |

\* cited by examiner

SURGICAL END EFFECTOR ADJUNCT ATTACHMENT

FIELD

Methods and devices are provided for securing one or more adjunct materials to an end effector of a surgical instrument.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having an end effector with a pair of movable opposed jaws for engaging and stapling tissue. The staples are typically contained in a staple cartridge, which can house multiple rows of staples and that is often disposed in one of the jaws for ejection of the staples to the surgical site. In use, the jaws are positioned to engage tissue, and the device is actuated to eject staples through the tissue. Some staplers include a knife configured to travel between rows of staples in the staple cartridge to longitudinally cut the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for improved devices and methods for stapling tissue, blood vessels, ducts, shunts, or other objects or body parts such that leaking and inflammation is minimized while substantially maintaining the natural characteristics of the treatment region.

SUMMARY

Methods, systems, and devices are provided for releasably retaining an adjunct to a jaw of an end effector of a surgical instrument. In one embodiment, an end effector is provided and can include upper and lower jaws that are movably coupled to one another and configured to move between open and closed configurations for clamping tissue therebetween. The end effector can further include a cartridge having an inner tissue-facing surface with a plurality of staple cavities with staples disposed therein. The cartridge can be configured to releasably couple to the lower jaw. The end effector can further include an anvil assembly having an anvil plate with a plurality of staple forming pockets formed therein on an inner tissue-facing surface thereof. The anvil assembly can be configured to releasably couple to at least one of the cartridge and the upper jaw. The end effector can further include a first adjunct material releasably secured to the inner tissue-facing surface of the anvil plate and a first restraining element extending across the first adjunct material for securing the first adjunct to the anvil plate.

In one embodiment, a second adjunct material can be releasably secured to the inner tissue-facing surface of the cartridge and a second restraining element can extend across the second adjunct material for securing the second adjunct to the cartridge. The first restraining element can include a suture formed from a material selected from the group consisting of a thermoplastic material, a polydioxanone material, an elastic material, a biocompatible material, and combinations thereof. A terminal end of the restraining element can be fixedly attached to an attachment site formed on one of the anvil plate and the cartridge. In certain aspects, the attachment site can include a roughened surface region and/or the attachment site can be formed on one of a top surface of the anvil plate, a side surface of the anvil plate, a bottom surface of the cartridge, and a side surface of the cartridge.

In another embodiment, the end effector can include a pan coupled to the cartridge such that an inner surface of the pan applies a compressive force against opposed terminal ends of the second restraining element to secure the second restraining element to the cartridge. In certain aspects, the anvil plate can include at least one notch formed in a perimeter thereof and can be configured to prevent sliding of the first restraining element relative to the anvil plate. At least one of the cartridge and the lower jaw can include a notch formed therein and can be configured to prevent sliding of the second restraining element.

In one embodiment, the end effector can further include an alignment feature that extends outward from the anvil plate and can be configured to engage a complementary alignment feature on the upper jaw for aligning the anvil plate relative to the upper jaw. The coupling feature can be formed from an elastic material that is configured to bias the anvil plate to the open anvil configuration when the opposed jaws are in the open configuration.

In another embodiment, an end effector assembly is provided and can include a cartridge having an inner tissue-facing surface with a plurality of staple cavities with staples disposed therein. The cartridge can be configured to releasably couple to a lower jaw of an end effector of the surgical instrument. The end effector can further include an anvil assembly having an anvil plate with a plurality of staple forming pockets formed therein on an inner tissue-facing surface thereof. The anvil assembly can be configured to releasably couple to at least one of the cartridge and an upper jaw of the end effector. The end effector can further include a first adjunct material releasably secured to the inner tissue-facing surface of the anvil plate and a first restraining element extending across the first adjunct material for securing the first adjunct to the anvil plate.

Surgical methods are also provided, and in one embodiment the method includes releasably coupling an anvil assembly to at least one of an upper jaw of an end effector and a cartridge configured for coupling to a lower jaw of the end effector. The anvil assembly can include an anvil plate with a plurality of staple forming pockets formed therein on an inner tissue-facing surface thereof that correspond to a plurality of staple cavities along an inner tissue-facing surface of the cartridge. The inner tissue-facing surface facing of the anvil plate can have a first adjunct material releasably secured thereto by a first restraining element.

The details of one or more variations of the subject matter described herein are set forth in the accompanying drawings and the description below. Other features and advantages of the subject matter described herein will be apparent from the description and drawings, and from the claims.

BRIEF DESCRIPTION OF DRAWINGS

This invention will be more fully understood from the following detailed description taken in conjunction with the accompanying drawings, in which.

DETAILED DESCRIPTION

Figure 1:
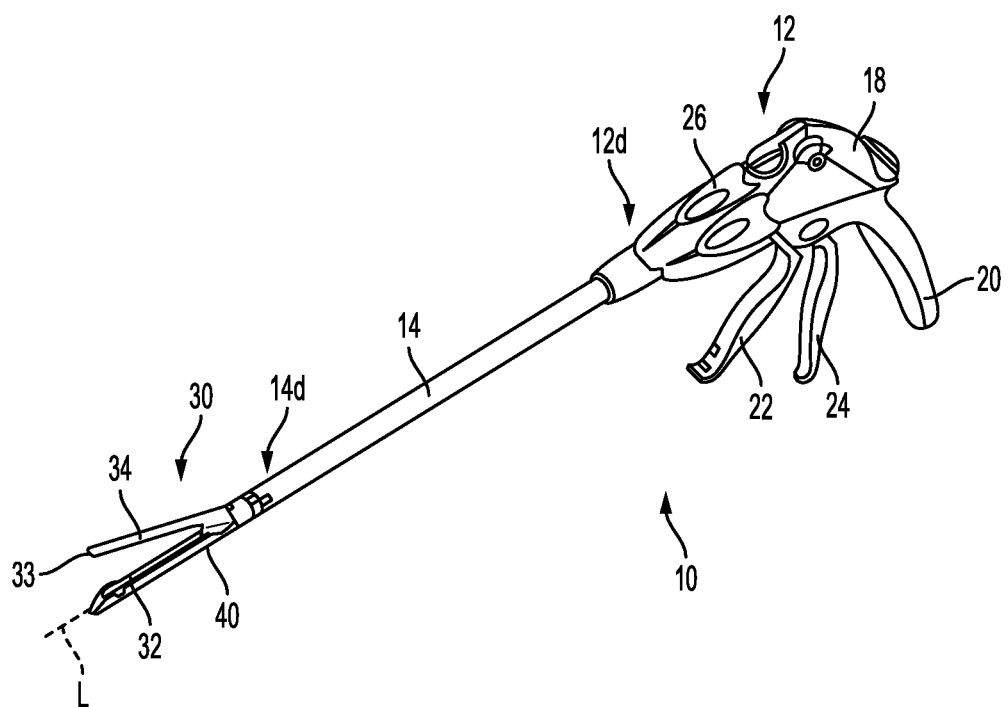
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the instrument can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s). Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing). In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety.

Surgical Stapling Instruments

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used in a variety of tissues in a variety of different surgical procedures, for example in thoracic surgery or in gastric surgery.

Figure 2:
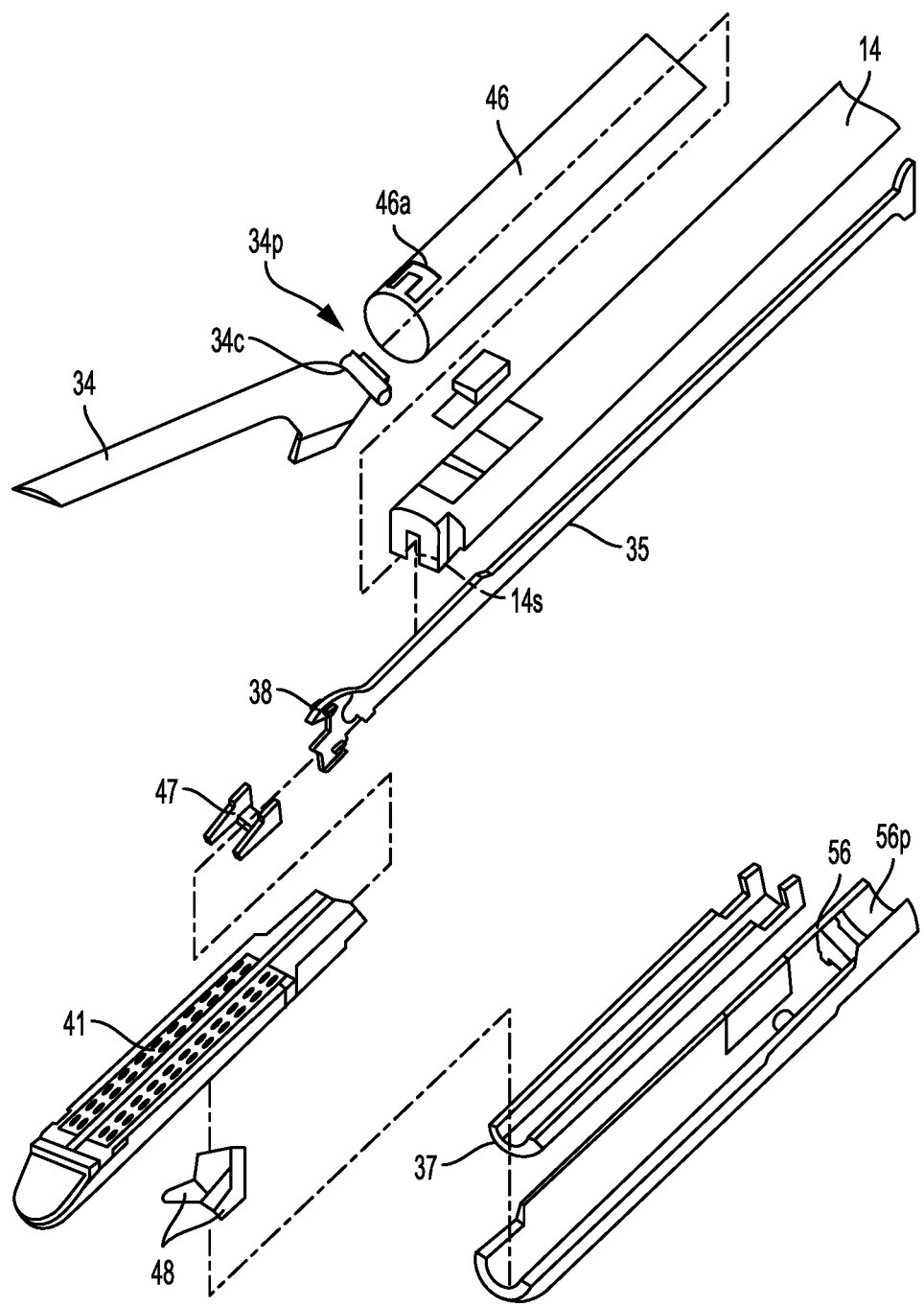
FIG. 2 is an exploded view of a distal portion of the surgical stapler of FIG. 1.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
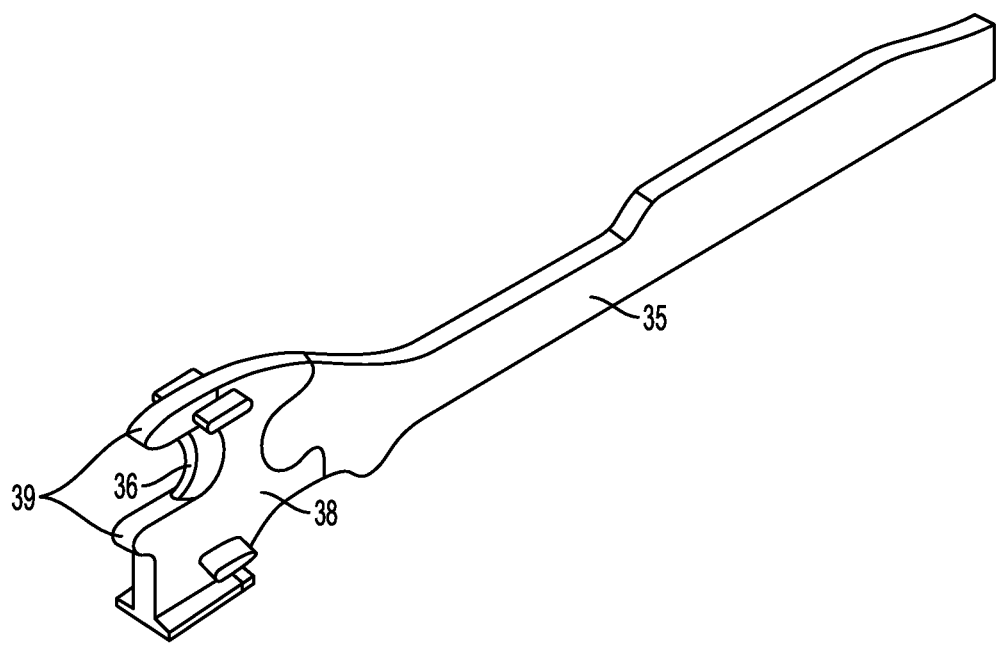
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32, 34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
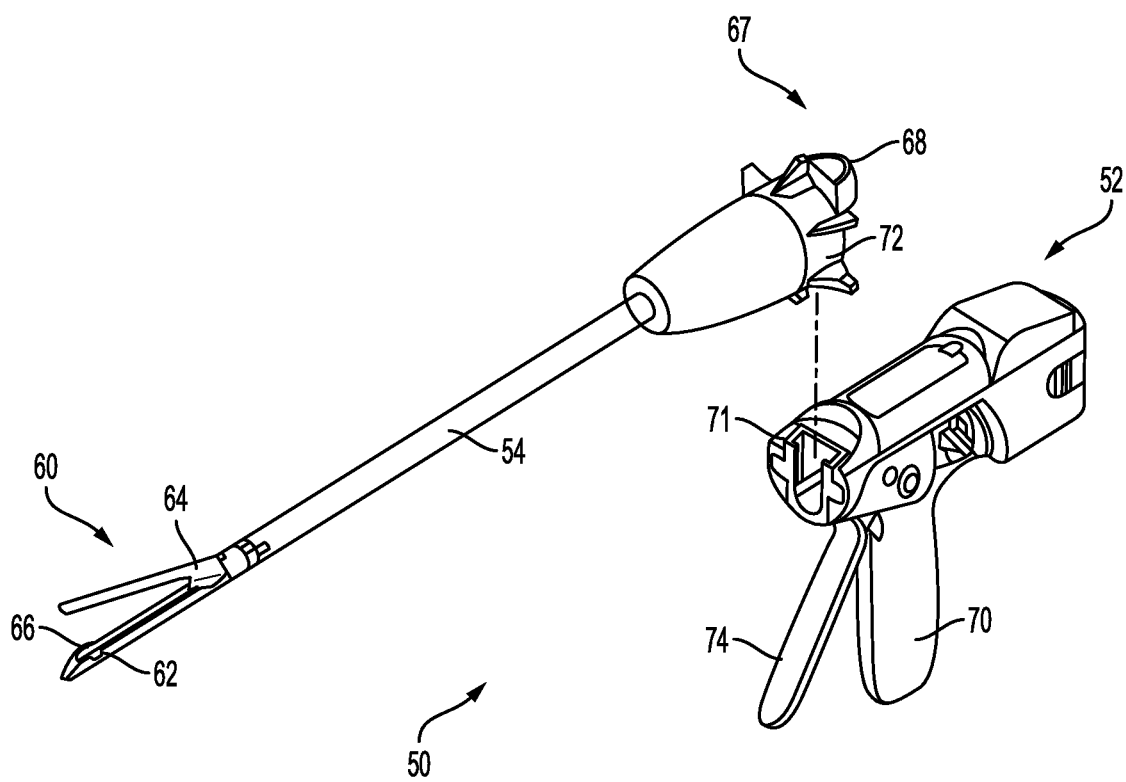
FIG. 4 is a perspective view of another embodiment of a surgical stapler having a modular shaft.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
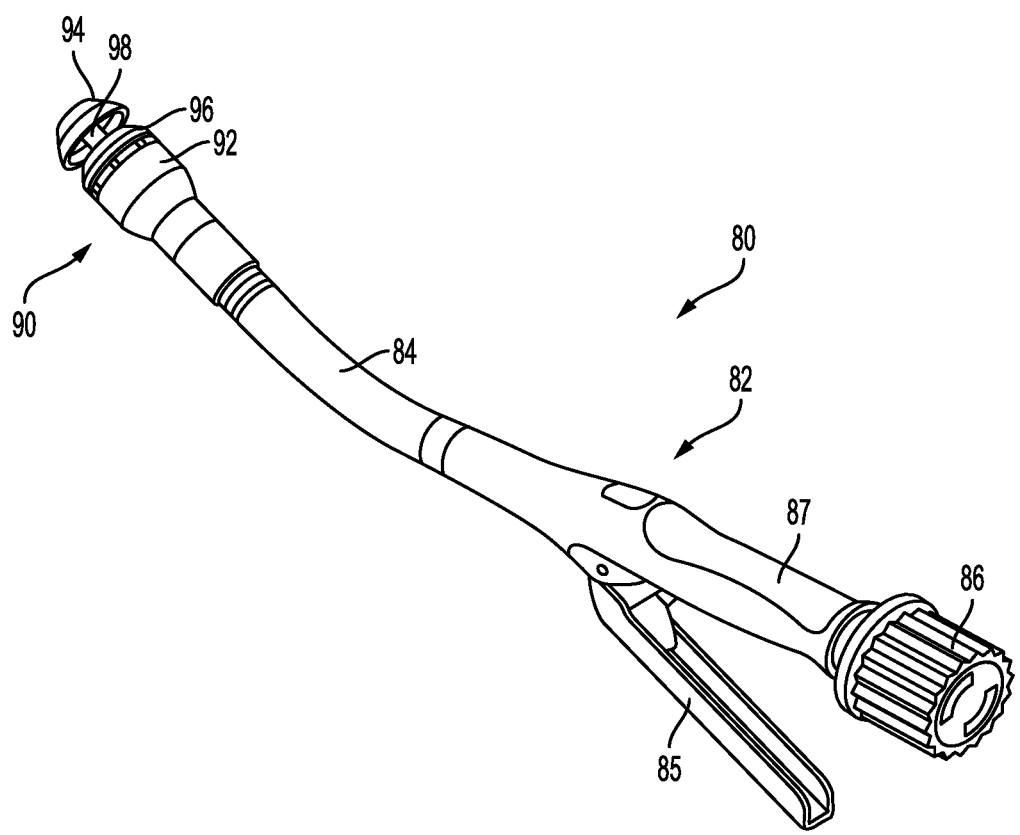
FIG. 5 is a perspective view of an embodiment of a circular surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft 98 can be disposed within the cartridge assembly 92 and extend distally outside of the cartridge assembly 92, terminating in a distal mating feature. The second portion of the shaft 98 can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, i.e. move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. Pat. Pub. No. 2015/0272575, entitled "Surgical Instrument Comprising a Sensor System," and filed on Mar. 26, 2014, and U.S. Pat. Pub. No. 2015/0351758, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be absorbed onto the film or bound to the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct. The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., a Z direction) such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue in-growth. The materials can include bioabsorbable and biocompatible polymers, including homopolymers and copolymers. Bioabsorbable polymers can be absorbable, resorbable, bioresorbable, or biodegradable polymers. An adjunct can also include active agents, such as active cell culture (e.g., diced autologous tissue, agents used for stem cell therapy (e.g., Biosutures and Cellerix S.L.), hemostatic agents, and tissue healing agents.

The adjuncts can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. patent application Ser. No. 14/840,613 entitled "Medicant Eluting Adjuncts and Methods of Using Medicant Eluting Adjuncts" and filed Aug. 31, 2015, which is hereby incorporated by reference in its entirety.

Adjunct Attachment

Various exemplary devices, systems and methods for releasably retaining an adjunct material on an end effector of a surgical instrument are described herein. In a typical surgical stapler end effector, the anvil has a preconfigured set of staple pockets formed therein and configured to receive and form staples fired from the cartridge. As a result, the end effector can only be used with staple cartridges having staple cavities that align with the anvil. Accordingly, in an exemplary embodiment, various anvil plates are provided having varying staple pocket configurations for use with different staple cartridges. The anvil plate can mate to the upper jaw of an end effector, and a cartridge designed for use with that particular anvil plate can be inserted into the lower jaw of the end effector. As such, the end effector can create a variety of staple configurations by switching out the anvil assembly and/or cartridge. Furthermore, adjunct materials can be releasably secured to either the cartridge or anvil plate using one or more restraining elements. For example, the adjunct materials can be pre-attached to the anvil plate and/or the cartridge (e.g., during manufacturing) and can be released from the anvil plate and/or cartridge during firing of the end effector (e.g., advancing a knife along the end effector to fire staples and cut tissue, adjunct material, and any restraining elements), as will be described in greater detail below.

Figure 6:
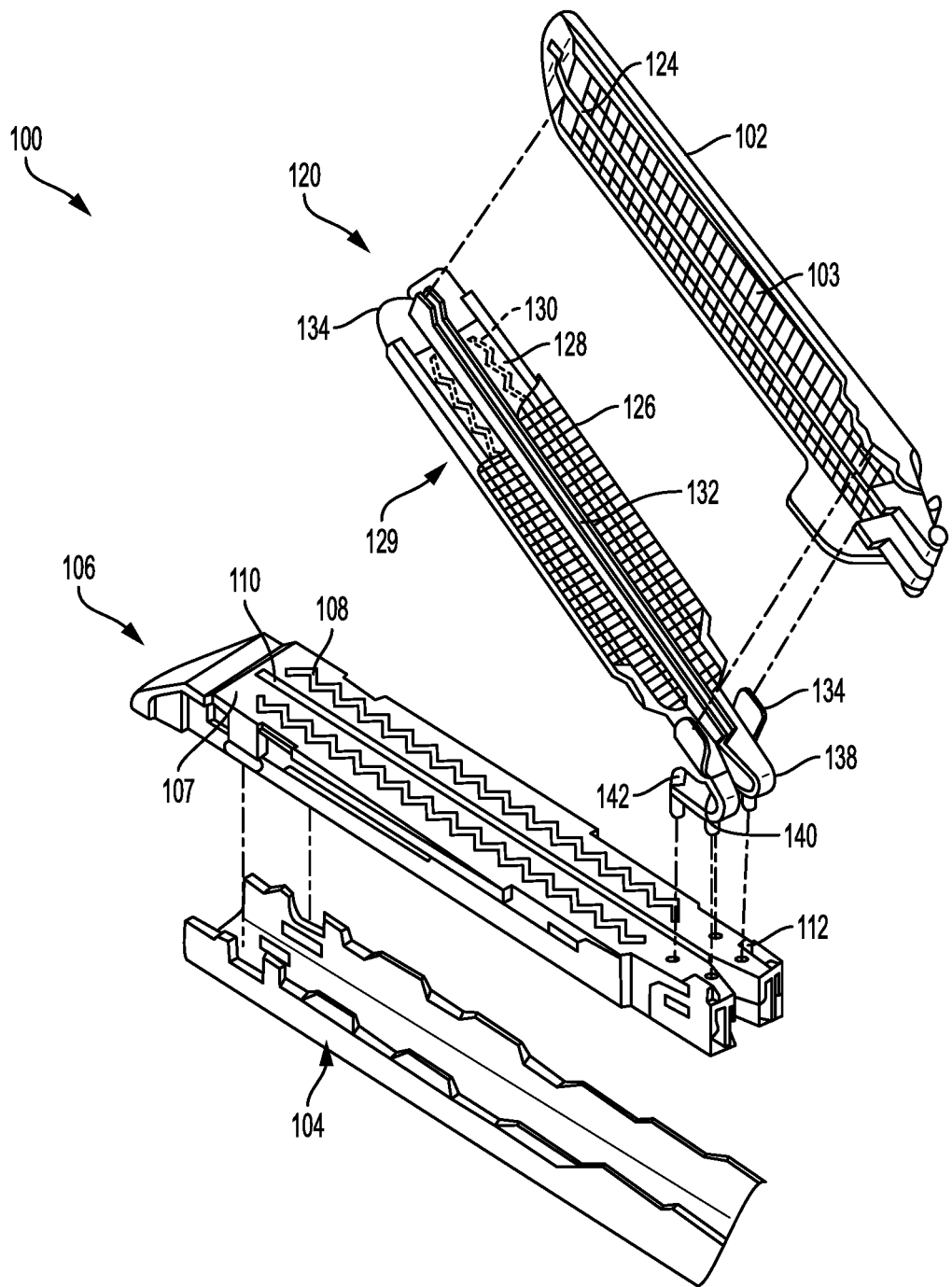
FIG. 6 is a partially exploded view of an end effector including a pair of opposed jaws and a cartridge.

FIG. 6 illustrates one embodiment of an end effector 100 including upper and lower jaws 102, 104, respectively, that can pivot between open and closed configurations. As shown in FIG. 6, a staple cartridge 106 can be configured to releasably couple to the lower jaw member 104, and can include staple cavities 108 having staples disposed therein. The upper jaw 102 can be in the form of an anvil having staple pockets 103 formed therein and configured to receive and form staples fired from the cartridge 106. Both the upper jaw 102 and cartridge 106 can include knife slots 124,110, respectively, configured to allow a knife to advance therealong.

As shown in FIG. 6, an anvil assembly 120 can be configured to releasably couple to an inward tissue-facing surface 107 of the cartridge 106 and/or an inward-facing surface 103 of the upper jaw 102. The anvil assembly 120 can include an anvil plate 128 having a rectangular shape that can extend along either the upper jaw 102 or cartridge 106. The anvil plate 128 can include an anvil adapter 126 along an outward-facing surface of the anvil plate 128. The anvil adapter 126 can include plate features configured to mate with jaw features along the inward-facing surface 103 of the upper jaw 102 (see, for example, FIG. 11) thereby assisting with securing the alignment between the anvil plate 128 and the upper jaw 102. The anvil plate 128 can further include staple pockets 130 (shown as imprints along an outward-facing surface of the anvil plate 128) that are recessed along an inward tissue-facing surface 129 of the anvil plate 128. The staple pockets 130 can be arranged along the anvil plate 128 such that each staple pocket 130 corresponds to a staple cavity 108 of the cartridge 106 for assisting with forming the staples (e.g., stapling tissue together and/or adjunct to tissue). The anvil plate 128 can include a knife channel 132 that extends longitudinally along the anvil plate 128 and that is configured to allow a knife to advance therealong.

In some embodiments, the anvil plate 128 can include one or more alignment features 134 that can assist with maintaining alignment between the anvil plate 128 and the upper jaw 102. For example, as shown in FIG. 6, the anvil plate 128 can include proximal and distal alignment features 134 that extend upward from the outward-facing surface of the anvil plate 128 toward the upper jaw 102. The alignment features 134 can be configured as tabs that mate with one or more recesses, slots, through-holes, etc., in the upper jaw 102. Depending on the configuration of the upper jaw 102, the alignment features 134 may slide longitudinally within the recesses, slots, through holes, etc., of the upper jaw 102 as the jaw members move between the open and closed positions thus maintaining alignment between the anvil plate 128 and the upper jaw 102 during opening and closing of the jaws. Additionally, the alignment features 134 can function to maintain alignment between the anvil plate 128 and the cartridge 106. Proper alignment between the anvil plate 128 and the cartridge 106 ensures that staples contact staple pockets 130, and form properly, when fired from the cartridge 106.

As shown in FIG. 6, the anvil assembly 120 can also include one or more attachment features 138 for coupling the anvil plate 128 to the cartridge 106, such as to the inward tissue-facing surface 107 of the cartridge 106. In some embodiments, as shown in FIG. 6, the attachment features 138 can include at least one bracket. The bracket can extend between the anvil plate 128 and cartridge 106 and can allow the anvil plate 128 to pivot (e.g., along with the upper jaw) between an open and closed configuration relative to the cartridge 106. In some embodiments, the attachment features 138 can function as a hinge and biasing element that biases the anvil plate 128 to the open configuration thereby allowing the anvil plate 128 to pivot and follow the upper jaw 102 when the jaws open.

The attachment features 138 of the anvil assembly 120, and the inward tissue-facing surface 107 of the cartridge 106, can include coupling features 140, 112, respectively. The coupling features 140, 112 can be in the form of through-holes that enable, for example, pins 142, rivets, or similar features, to extend therethrough and connect the coupling features 140 of the anvil assembly 120 to the coupling features 112 on the cartridge 106. This configuration allows the anvil plate 128 and cartridge 106 to be releasably coupled together thereby allowing the end effector to provide various stapling configurations by switching out either the cartridge 106 or anvil plate 128. As such, the cartridge 106 and anvil assembly 120 can provide an advantage over end effectors that are, for example, limited to the configuration of the staple pockets in the anvil.

Furthermore, it can be desirable for an end effector to include features and/or components that facilitate releasable attachment of an adjunct to the end effector. For example, an adjunct can be attached, including pre-attached during manufacturing or prior to a surgical procedure, to the end effector using a restraining element, such as a suture. In one embodiment, the suture can be elongated and made out of, for example, a thermoplastic such as polydioxanone (PDS), an elastic material, and/or any other biocompatible material suitable for securing the adjunct to the end effector. In some embodiments, the restraining element can be continuous or non-continuous with opposing ends of the restraining element anchored to a part of the anvil assembly and/or cartridge. When the stapler is fired, staples can fire through the tissue and adjunct toward the anvil to be formed. A knife can travel through knife channels in the cartridge, anvil plate, and upper jaw thereby cutting the restraining element and releasing the adjunct from the end effector to allow the adjunct to remain at the surgical site.

Figure 7:
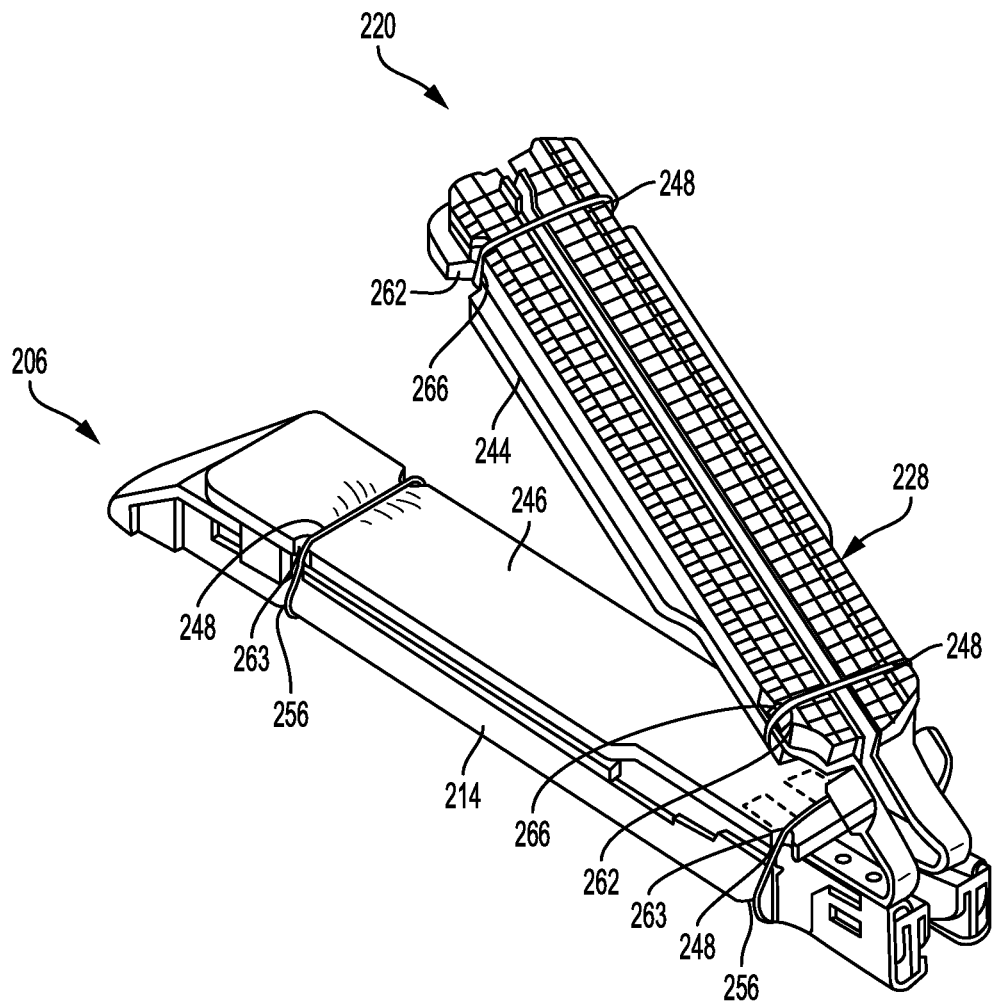
FIG. 7 is a perspective view of another embodiment of an end effector having an anvil assembly coupled to a cartridge with an adjunct secured to the anvil assembly and an adjunct secured to the cartridge.

FIG. 7 illustrates an anvil assembly 220 releasably coupled to a cartridge 206 with a first adjunct material 244 coupled to an inward tissue-facing surface of an anvil plate 228 of an anvil assembly 220, and a second adjunct material 246 coupled to an inward tissue-facing surface of the cartridge 206. The first and second adjuncts 244, 246 can each be secured to the anvil assembly 220 and cartridge 206, respectively, using one or more restraining elements or sutures 248. Each suture 248 can extend around the first adjunct 244 and anvil plate 228 or around the second adjunct 246 and cartridge 206, thereby securing the first or second adjuncts 244, 246 to the respective anvil plate 228 or cartridge 206.

As shown in FIG. 7, the cartridge 206 and/or a cartridge pan 214 (coupled to the cartridge 206) can include one or more cartridge notches 256, and the anvil plate 228 of the anvil assembly 220 can include one or more anvil notches 266. For example, the notches 256, 266 can be shaped as curved recesses and can be configured to allow a part of the suture 248 to sit therein for maintaining a position of the suture 248 relative to either the anvil plate 228 or cartridge 206. The notches 256, 266 can thus assist with preventing the suture 248 from slipping and unsecuring a position of either the first or second adjunct 244, 246 relative to the anvil plate or cartridge, respectively.

For example, the first adjunct 244 can be secured to an inward tissue-facing surface of the anvil plate 228 by a pair of sutures 248 (e.g., one suture 248 positioned adjacent at a distal end of the anvil plate 228 and one suture 248 positioned adjacent a proximal end of the anvil plate 228) that wrap around the first adjunct 244 and anvil plate 228. As shown in FIG. 7, portions of the proximally and distally positioned sutures 248 can be positioned in anvil notches 266 along a side of the anvil plate 228. The notches 266 can prevent the sutures 248 from shifting or slipping longitudinally along the anvil plate 228, thereby ensuring that the sutures 248 secure the first adjunct to the anvil plate 228.

Similarly, the second adjunct 246 can be secured to an inward tissue-facing surface of the cartridge 206 by a pair of sutures 248 (e.g., one suture 248 positioned adjacent a distal end of the cartridge 206 and one suture 248 positioned adjacent a proximal end of the cartridge 206) that wrap around the second adjunct 246 and cartridge 206. As shown in FIG. 7, portions of the proximally and distally positioned sutures 248 can be positioned in cartridge notches 256 along a side of the cartridge 206 and/or cartridge pan 214. The cartridge notches 256 can prevent the sutures 248 from shifting or slipping longitudinally along the cartridge 206 thereby ensuring that the sutures 248 secure the second adjunct 246 to the cartridge 206.

As shown in FIG. 7, the first adjunct 244 can include first adjunct notches 262 along opposing sides of the first adjunct 244, and the second adjunct 246 can include second adjunct notches 263 along opposing sides of the second adjunct 246. The first and second adjuncts 244, 246 can be made of the same material, or they can be made of different materials. The first adjunct notches 262 can be positioned along the first adjunct 244 such that first adjunct notches 262 align with the anvil notches 266 when the first adjunct 244 is properly aligned with the anvil plate 228 (e.g., the adjunct surface area of the first adjunct covers the inward tissue-facing surface of the anvil plate 228). As such, when the suture 248 extends around the first adjunct 244 and anvil plate 228 and along the first adjunct notches 262 and anvil notches 266, the suture 248 secures a desired positioning between the first adjunct 244 and the anvil plate 228. Similarly, the second adjunct notches 263 can be positioned along the second adjunct 246 such that the second adjunct notches 263 align with the cartridge notches 256 when the second adjunct 246 is properly aligned with the cartridge 206 (e.g., the second adjunct surface area of the second adjunct covers the inward tissue-facing surface of the cartridge 206). As such, when the suture 248 extends around the second adjunct 246 and cartridge 206 and along the second adjunct notches 263 and cartridge notches 256, the suture 248 secures a desired positioning between the second adjunct 246 and the cartridge 206. Each of the sutures 248 can be made of the same material, or one or more of the sutures 248 can be made of a different material.

Although the cartridge notches 256, anvil notches 266, and first and second adjunct notches 262, 263 are shown as U-shaped cutouts, any one of the cartridge notches 256, anvil notches 266, and first and second adjunct notches 262, 263 can have any number of shapes and/or sizes that allow a part of suture to extend therealong for securing the suture in position relative to either the anvil plate 228 or cartridge 206. For example, any one of the cartridge notches 256, anvil notches 266, and first and second adjunct notches 262, 263 can be V-shaped, squared, or any other geometry. Furthermore, any number of notches (e.g., cartridge notches 256, anvil notches 266, and first and second adjunct notches 262, 263) and lengths of suture 248 can be used to secure the position of either the first or second adjuncts 244, 246. Alternatively, rather than notches 256, 266, the cartridge 206, cartridge pan 214, and/or the anvil plate 228, can include holes through which sutures 248 can be threaded. Similarly, the adjuncts 244, 246 can include holes that align with holes on the cartridge 206, cartridge pan 214, and/or anvil plate 228. Sutures can be threaded through the holes in the adjuncts 244, 246 and through the holes in the cartridge 206, cartridge pan 214, and/or the anvil plate 228, to retain the adjuncts 244, 246 on inward tissue-facing surfaces of the cartridge 206 and the anvil plate 228.

In some embodiments, it can be desirable to angle a suture extending around the adjunct material and cartridge to ensure that the adjunct is detached from the cartridge after at least one staple has been deployed (e.g., thereby securing the adjunct to the tissue).

Figure 8:
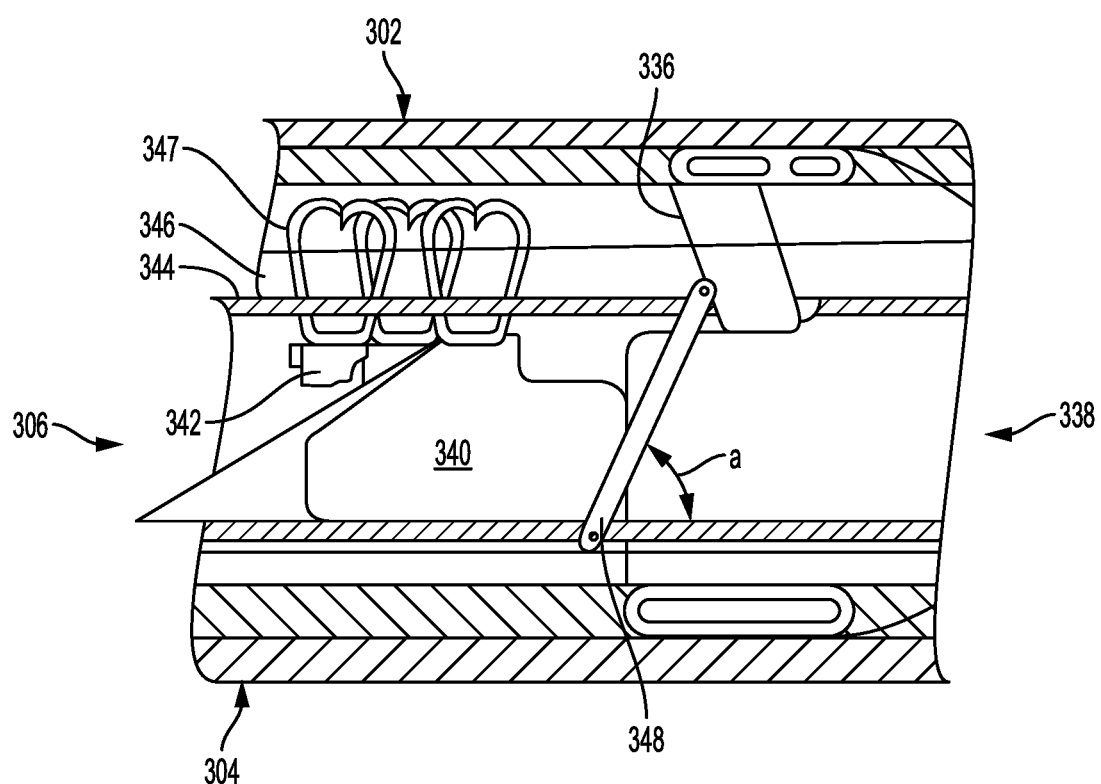
FIG. 8 is a cross-sectional view of one embodiment of an end effector having an adjunct material secured to a cartridge with a suture that extends around the cartridge.

FIG. 8 illustrates upper and lower jaws 302, 304 in a closed configuration, clamped around tissue 346, with an adjunct 344 secured to an inward tissue-facing surface of a cartridge 306 that is seated within the lower jaw 304. As shown in FIG. 8, the adjunct 344 is secured to the cartridge 306 using a suture 348 that extends around the adjunct 344 and cartridge 306 at an angle (a). For example, the suture 348 can extend along the adjunct 344 at a location proximal to the location at which the suture 348 extends around the back side of the cartridge 306. As such, as shown in FIG. 8, a side view of the suture 348 extending around the adjunct 344 and cartridge 306 shows the suture 348 extending at an angle (a) across the side of the cartridge 306. As illustrated in FIG. 8, a knife 338 can be configured to advance along the cartridge 306 to cut the tissue 346, suture, 348, and adjunct 344, using a knife blade 336. The knife 338 can also be configured to drive staples 347 from the cartridge 306 as it advances along the cartridge 306. As the knife advances along the length of the cartridge 306, it can push a wedge sled 340, which can push staple drivers 342 that hold staples 347 in a tissue-facing direction to form the staples 347. The angling of the suture 348 can ensure that the suture 348 is in a position to be cut without being stapled to the tissue 346. The angled suture 348 can be positioned such that the knife blade 336 is the first part of the knife 338 that contacts the suture 348 in order to cause the angled suture 348 to be cut approximately upon contact with the knife 338.

Alternatively or in addition to using continuous restraining elements, such as continuous sutures or lengths of suture that couple end to end, one or more non-continuous restraining elements that anchor opposing ends of the restraining elements to components of the cartridge and/or anvil assembly can be used.

Figure 9A:
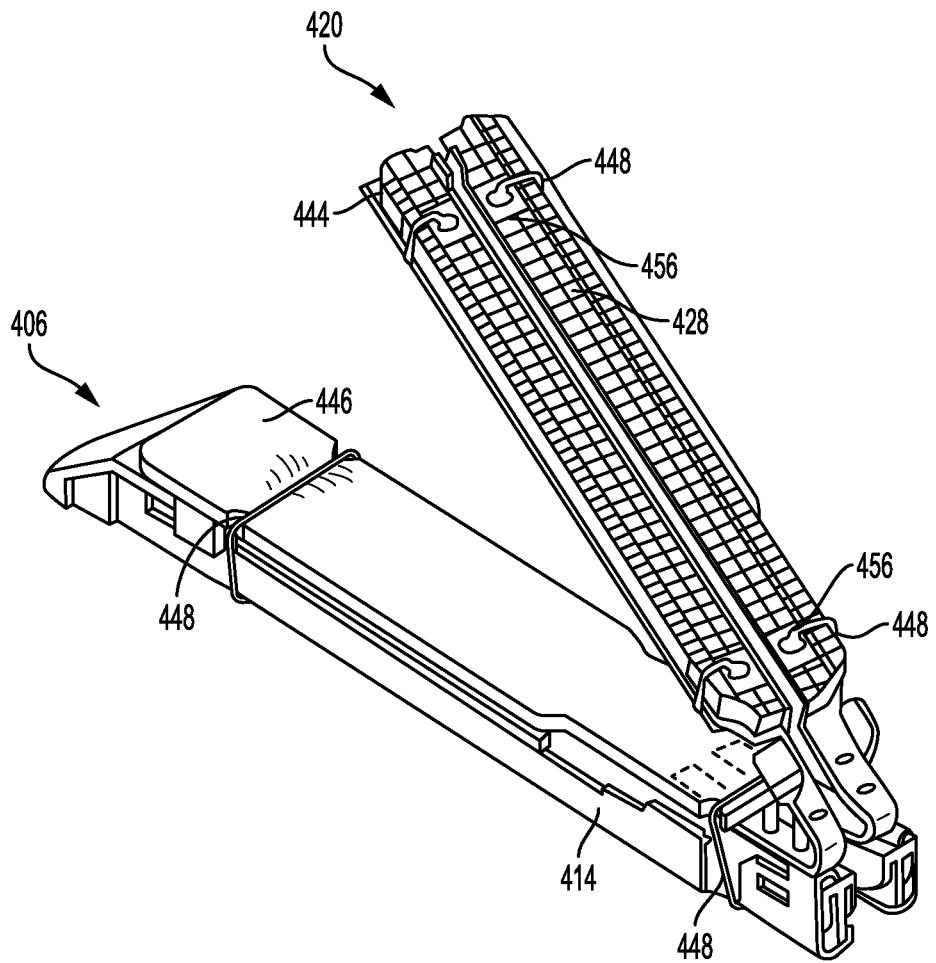
FIG. 9A is a perspective view of another embodiment of an end effector having an anvil assembly coupled to a cartridge with an adjunct secured to an anvil plate of the anvil assembly and an adjunct secured to the cartridge using at least one suture.
Figure 9B:
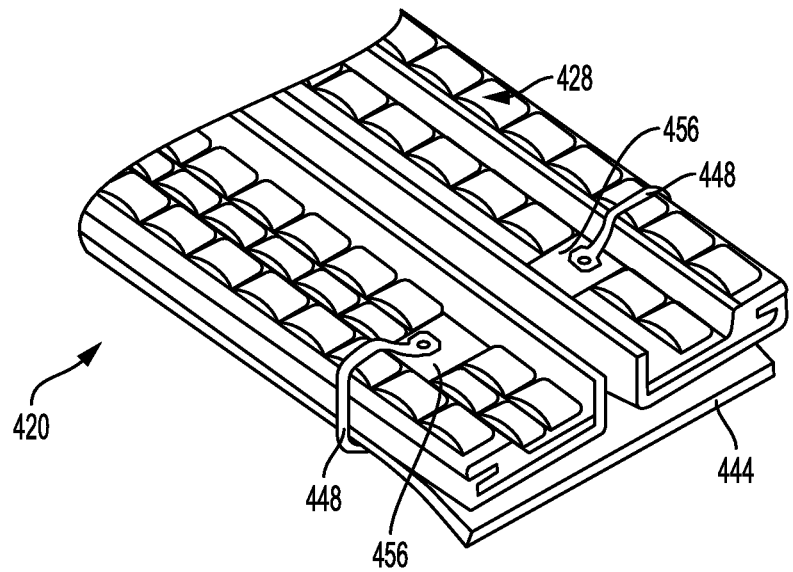
FIG. 9B is a top perspective view of a portion of the anvil plate of FIG. 9A showing suture attachment points along the top surface of the anvil plate.
Figure 9C:
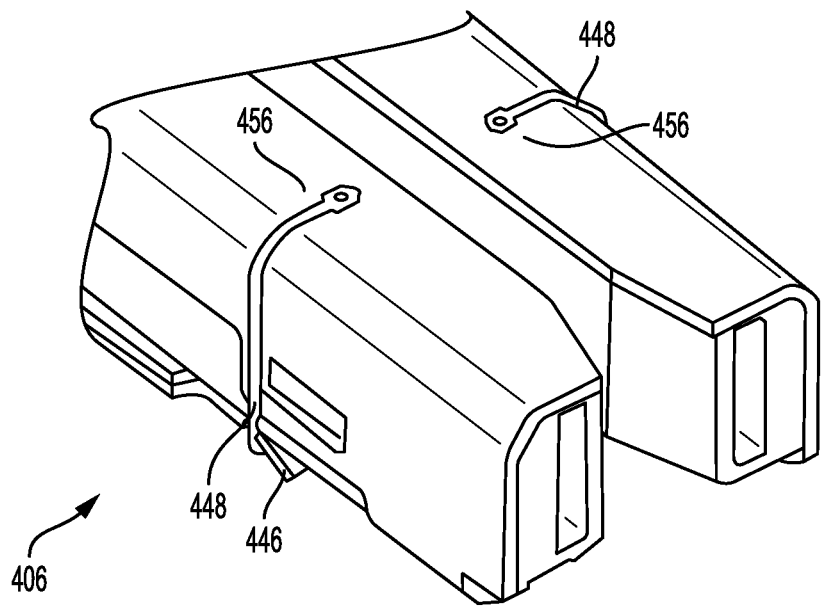
FIG. 9C is a bottom perspective view of a portion of the cartridge of FIG. 9A showing the suture attachment points along the underside of the cartridge.

FIGS. 9A-9C illustrate another embodiment of an anvil assembly 420 releasably coupled to a cartridge 406 with a cartridge pan 414 coupled to a bottom side of the cartridge 406. As shown in FIGS. 9A-9C, a first adjunct material 444 can be coupled to an inward tissue-facing surface of the anvil plate 428 of the anvil assembly 420 and a second adjunct material 446 can be coupled to an inward-tissue facing surface of the cartridge 406. The first and second adjuncts 444 and 446 can be secured to the anvil assembly 420 and cartridge 406 with one or more sutures 448. Furthermore, the anvil assembly 420 and/or cartridge 406 can include one or more suture attachment sites 456 that are configured to couple a part (e.g., opposing ends) of the suture 448 thereto. As shown in FIGS. 9B and 9C, at least one pair of attachments sites 456 can be positioned along an outward-facing surface of the anvil plate 428 of the anvil assembly 420 (as shown in FIGS. 9A and 9B), and another pair of attachment sites 456 can be positioned along an outward-facing surface of the cartridge 406 and/or an outward-facing surface of the cartridge pan 414 (as shown in FIG. 9C).

The suture 448, and more particularly each of the opposing ends of the suture 448, can be heat staked, welded, or otherwise adhered to the attachment sites 456. In some implementations, the attachment site 456 can include a texture that assists with securing the suture 448 to the attachment site. For example, the attachment site 456 can be roughened or otherwise made to include a textured surface. The cartridge 406 and/or anvil assembly 420 can include one or more attachment site 456, and each attachment site 456 can include any of a variety of sized and shaped surface areas. For example, the attachment sites 456 can have various shapes, such as circular, triangular, or any other shaped surface area. Additionally, some attachment sites 456 can be coated with a material that improves the attachment of the suture 448. Alternatively or in addition, small posts, barbs or hooks can be used at the attachment sites 456 to secure the suture 448 in place. Although two sutures 448 and two pairs of attachment sites 456 are used to secure each adjunct 444, 446 in FIGS. 9A-9C, any number of sutures and attachment sites can be used to secure the adjuncts to the anvil plate and/or cartridge.

Figure 10A:
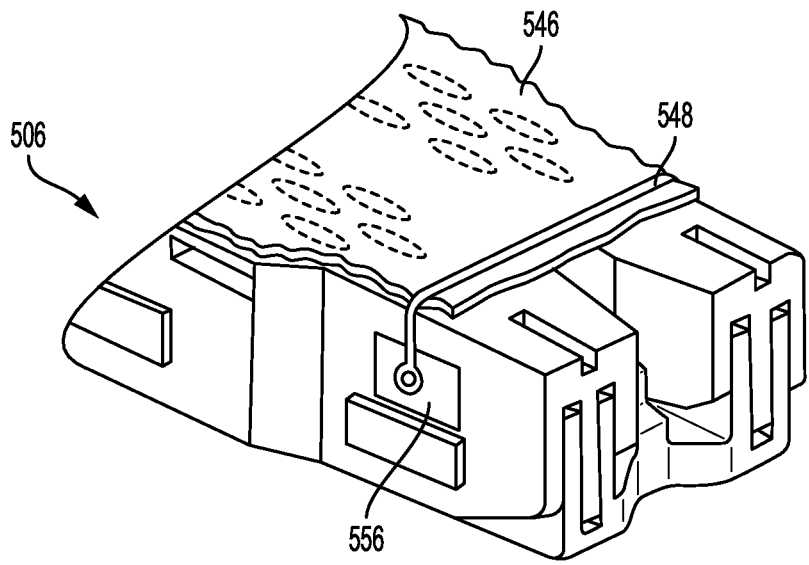
FIG. 10A is a perspective view of a portion of a cartridge having suture attachment points on opposed sides of the cartridge according to another embodiment.
Figure 10B:
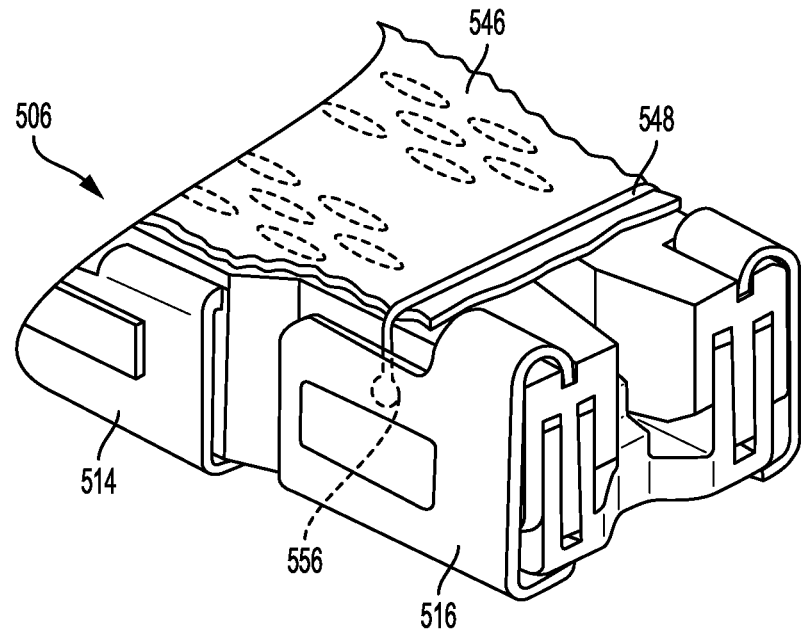
FIG. 10B is a perspective view of the portion of the cartridge of FIG. 10A showing a pan coupled to the cartridge and positioned over the suture attachment points.

FIGS. 10A-10B illustrate another embodiment of a suture 548 extending across a second adjunct 546 for securing the second adjunct 546 to a cartridge 506. As shown in FIG. 10A, opposed ends of the suture can be secured to attachment sites 556 positioned along opposed sides of the cartridge 506. More than one suture 548 can be secured across the second adjunct and secured to attachment sites 556 positioned on opposed sides of the cartridge 506 or lower jaw 514. Similarly, opposed ends of suture can be secured to attachment sites positioned along opposed sides of the anvil plate or other part of the anvil assembly.

Additionally or alternatively, as shown in FIG. 10B, a pan 516 can be releasably coupled to the cartridge 506 such that an inner surface of the pan 516 can provide a compressive force against the ends of the suture 548, thereby further securing the coupling between the ends of the suture 548 and the attachment sites 556. The pan 516 can also protect the ends of the suture 548 from being dislodged from the cartridge 506 as the cartridge 506 is inserted into a channel of a lower jaw of an end effector. Various other components can be coupled to either the cartridge and/or anvil plate for providing additional securing forces at the point of attachment between the suture and attachment sites, which are within the scope of the is disclosure.

Figure 11:
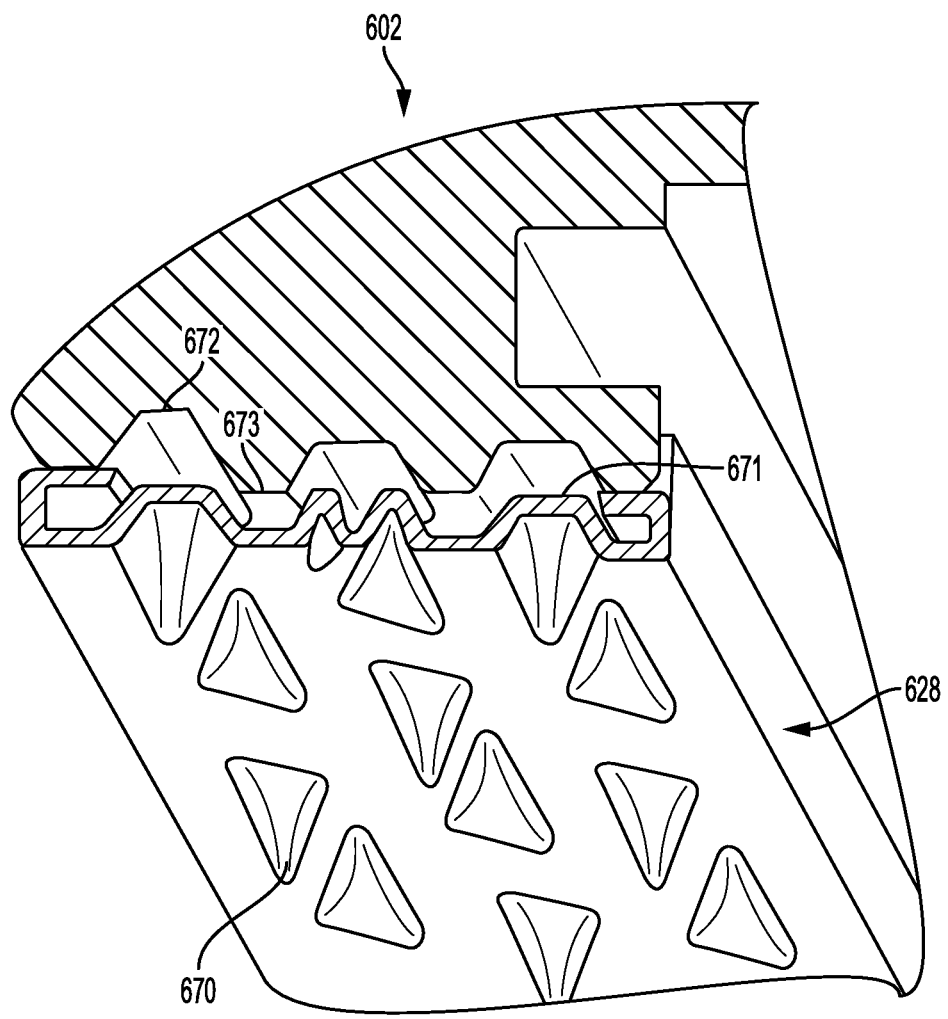
FIG. 11 is a cross-sectional view of an anvil plate having anvil surface features that mate with upper jaw cavities along an upper jaw member of an end effector according to yet another embodiment.

FIG. 11 illustrates anvil features 670 that can extend from an outward-facing surface 671 of the anvil plate 628 and that are configured to mate with jaw features 672 (e.g., cavities) that extend into an inward-facing surface 673 of the upper jaw 602. The anvil features 670 can have a similar shape as the jaw features 672 such that, when mated, the outward-facing surface of the anvil plate 628 can be restricted from sliding against the inward-facing surface of the upper jaw 602, thereby assisting with maintaining a preferred alignment between the anvil plate 628 and the upper jaw 602. The anvil features 670 and/or jaw features 672 can include stamped metal and/or elastomer and can have any number of a variety of shapes and sizes. Furthermore, it is within the scope of this disclosure for the cartridge and/or lower jaw to include features that mate with corresponding features along the lower jaw for assisting with maintaining a desired position of the cartridge relative to the lower jaw.

A person skilled in the art will appreciate that the present invention has application in conventional minimally-invasive and open surgical instrumentation as well application in robotic-assisted surgery. Furthermore, the devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. An end effector for a surgical instrument, comprising:
   upper and lower jaws movably coupled to one another and configured to move between open and closed configurations for clamping tissue therebetween, the upper jaw having a knife slot configured to allow a knife to advance therealong;
   a cartridge having an inner tissue-facing surface with a plurality of staple cavities with staples disposed therein, the cartridge being configured to releasably couple to the lower jaw;
   an anvil assembly having a detachable anvil plate with a plurality of staple forming pockets formed therein on an inner tissue-facing surface thereof, the anvil assembly being releasably coupled to the cartridge and configured to releasably couple to the upper jaw;
   a first adjunct material releasably secured to the inner tissue-facing surface of the detachable anvil plate; and
   a first restraining element extending across the first adjunct material and at least a portion of a top surface of the detachable anvil plate for securing the first adjunct to the detachable anvil plate, the top surface being opposite of the inner tissue-facing surface of the detachable anvil plate.

2. The end effector of claim 1, further comprising:
   a second adjunct material releasably secured to the inner tissue-facing surface of the cartridge; and
   a second restraining element extending across the second adjunct material for securing the second adjunct to the cartridge.

3. The end effector of claim 2, wherein a terminal end of the second restraining element is fixedly attached to an attachment site formed on one of a bottom surface of the cartridge and a side surface of the cartridge.

4. The end effector of claim 2, further comprising a pan coupled to the cartridge such that an inner surface of the pan applies a compressive force against opposed terminal ends of the second restraining element to secure the second restraining element to the cartridge.

5. The end effector of claim 1, wherein the detachable anvil plate includes at least one notch formed in a perimeter thereof and configured to prevent sliding of the first restraining element relative to the detachable anvil plate.

6. The end effector of claim 2, wherein at least one of the cartridge and the lower jaw includes a notch formed therein and configured to prevent sliding of the second restraining element.

7. The end effector of claim 1, further comprising an alignment feature extending outward from the detachable anvil plate and configured to engage a complementary alignment feature on the upper jaw for aligning the detachable anvil plate relative to the upper jaw.

8. The end effector of claim 1, further comprising a coupling feature on the anvil assembly and configured to move the detachable anvil plate between an open anvil configuration and a closed anvil configuration relative to the cartridge.

9. The end effector of claim 8, wherein the coupling feature is formed from an elastic material that is configured to bias the detachable anvil plate to the open anvil configuration when the opposed jaws are in the open configuration.

10. The end effector of claim 1, wherein the first restraining element comprises a suture formed from a material selected from the group consisting of a thermoplastic material, a polydioxanone material, an elastic material, a biocompatible material, and combinations thereof.

11. The end effector of claim 1, wherein a terminal end of the first restraining element is fixedly attached to an attachment site formed on the detachable anvil plate.

12. The end effector of claim 11, wherein the attachment site comprises a roughened surface region.

13. The end effector of claim 11, wherein the attachment site is formed on one of the top surface of the detachable anvil plate and a side surface of the detachable anvil plate.

14. An end effector assembly for a surgical instrument, comprising:
   a cartridge having an inner tissue-facing surface with a plurality of staple cavities with staples disposed therein, the cartridge being configured to releasably couple to a lower jaw of an end effector of the surgical instrument;
   an anvil assembly having an anvil plate with a plurality of staple forming pockets formed therein on an inner tissue-facing surface thereof, the anvil assembly being directly and releasably coupled to the cartridge and configured to releasably couple to an upper jaw of the end effector, wherein the anvil plate has at least one first coupling feature, and the cartridge has at least one second coupling feature configured to releasably couple to the at least one first mating feature;

a first adjunct material releasably secured to the inner tissue-facing surface of the anvil plate; and a first restraining element extending across the first adjunct material and at least a portion of a top surface of the anvil plate for securing the first adjunct to the anvil plate, the top surface being opposite of the inner tissue-facing surface of the anvil plate.

15. The end effector assembly of claim 14, further comprising:

a second adjunct material releasably secured to the inner tissue-facing surface of the cartridge; and a second restraining element extending across the second adjunct material for securing the second adjunct to the cartridge.

16. The end effector assembly of claim 15, wherein a terminal end of the first restraining element is fixedly attached to an attachment site formed on the anvil plate and the second restraining element is fixedly attached to an attachment site formed on the cartridge.

17. The end effector assembly of claim 15, further comprising a pan coupled to the cartridge such that an inner surface of the pan applies a compressive force against opposed terminal ends of the second restraining element to secure the second restraining element to the cartridge.

18. The end effector assembly of claim 15, wherein the cartridge includes a notch formed therein and configured to prevent sliding of the second restraining element.

19. The end effector assembly of claim 14, wherein the anvil plate includes at least one notch formed in a perimeter thereof and configured to prevent sliding of the first restraining element relative to the anvil plate.

* * * * *